(12) United States Patent
Jackson et al.

(10) Patent No.: US 6,784,186 B1
(45) Date of Patent: Aug. 31, 2004

(54) THERAPEUTIC COMPOUNDS

(76) Inventors: Roy W. Jackson, 30 Through Road, Burwood, Victoria 3125 (AU); Kamani R. Subasinghe, 11 Ilora Court, Glen Waverley, Victoria 3150 (AU); Alan L. A. Boura, c/o Monash University, Dept. of Pharmacology, Wellington Road, Clayton, Victoria 3168 (AU)

(*) Notice: Subject to any disclaimer, the term of this patent is extended or adjusted under 35 U.S.C. 154(b) by 0 days.

(21) Appl. No.: 09/582,059

(22) PCT Filed: Jan. 29, 1999

(86) PCT No.: PCT/AU99/00062

§ 371 (c)(1),
(2), (4) Date: Nov. 20, 2000

(87) PCT Pub. No.: WO99/38869

PCT Pub. Date: Aug. 5, 1999

(30) Foreign Application Priority Data

Jan. 29, 1998 (AU) ............................................. PP1530
Apr. 21, 1998 (AU) ............................................. PP3114
Aug. 4, 1998 (AU) ............................................. PP5046

(51) Int. Cl.$^7$ ............... A61K 31/485; C07D 489/02; C07D 489/12; C07D 221/28; C07D 211/64

(52) U.S. Cl. ............... 514/279; 514/282; 514/286; 514/295; 514/307; 514/330; 546/39; 546/44; 546/45; 546/46; 546/63; 546/97; 546/149; 546/225; 546/228

(58) Field of Search ............... 546/39, 44, 45, 546/46, 63, 97, 149, 225, 228; 514/279, 282, 286, 295, 307, 330

(56) References Cited

U.S. PATENT DOCUMENTS

| | | | |
|---|---|---|---|
| 3,341,538 A | | 9/1967 | Block et al. |
| 3,928,359 A | | 12/1975 | Walther et al. |
| 3,950,346 A | * | 4/1976 | Atsumi et al. .......... 260/293.54 |
| 4,108,857 A | * | 8/1978 | Albertson .............. 260/293.54 |
| 5,610,283 A | | 3/1997 | Buechler |
| 5,977,326 A | * | 11/1999 | Scheinmann et al. ........ 536/4.4 |

FOREIGN PATENT DOCUMENTS

| | | |
|---|---|---|
| EP | 0 004 960 | 10/1979 |
| FR | 2 296 420 | 7/1976 |
| JP | 49-072261 A2 * | 7/1974 |
| WO | 94-01102 A1 * | 1/1994 |
| WO | WO 95/18186 | 7/1995 |

OTHER PUBLICATIONS

Maeda M and Tsuji A. H, Pharmacobio–Dyn. (1981), 4(3), 167–74.*

Uwaydah IM et al. J. Med. Chem. (1979), 22(7), 889–90.*

Yokoyama N et al. J. Med. Chem. (1979), 22(5), 537–53.*

Jackson WR et al. Clin. Exp. Pharmacol. Physiol. (1992), 19(1), 17–23.*

Greene TW and Wuts PGM. Protective Groups in Organic Synthesis. Second Edition, John Wiley and Sons. Inc. New York. pp. 12, 77.*

* cited by examiner

*Primary Examiner*—Evelyn Mei Huang (57) ABSTRACT

This invention relates to novel structural analogues and derivatives of compounds with general analgesic or related pharmacological activity. In particular the invention relates to derivatives of opioid compounds, particularly morphine and related compounds, in which an opioid compound is linked via the nitrogen at position 17 to a spacer group, which in turn is linked to a charged group, or a pharmaceutically acceptable salt thereof. In particularly preferred embodiments the opioid compound is morphine, codeine, or buprenorphine.

22 Claims, 3 Drawing Sheets

THERAPEUTIC COMPOUNDS

This application is a 371 of PCT/AU99/00062, filed on Jan. 29, 1999.

This invention relates to novel structural analogues and derivatives of compounds with general analgesic or related pharmacological activity. In particular the invention relates to derivatives of opioid compounds, particularly morphine and related compounds.

BACKGROUND OF THE INVENTION

A large range of therapeutic compounds is currently used in the treatment of conditions such as allergies, diarrhoea, migraine and other pain conditions, and in the treatment of congestive heart failure. These compounds include compounds with analgesic or related activities, such as anti-tussives, anti-depressants, local anaesthetics, anti-hypertensives, anti-asthmatics, anti-histamines, and anti-serotonins.

However, many of the therapeutic compounds of the types enumerated above have undesirable side-effects, such as the respiratory depression caused by opiates. In particular, many drugs which are useful for their action on the peripheral nervous system have undesirable effects in the central nervous system.

Thus opiates are the most powerful analgesics known, but their usefulness is greatly limited by their side-effects, including severe respiratory depression, and ability to induce addiction and physical dependence.

Despite intensive efforts to design analogues of morphine and related opioids which retain the analgesic activity but which do not have a deleterious effect on the central nervous system and the bowel, success has been limited. Structure-activity relationships have been extensively investigated, and a number of features have been widely accepted as essential. See for example "An Introduction to Pharmacology" by J. J. Lewis (E. & S. Livingston Ltd, 1964 Pages 401–407), and "Principles of Drug Action: The Basis of Pharmacology (Ed. W. B. Pratt and P. Taylor; Churchill Livingstone, $3^{rd}$ edition, 1990, Pages 25–27). In particular, it is generally considered that to retain analgesic activity the group on the tertiary nitrogen should be small, and should preferably be methyl; larger substituents are likely to be opiate receptor antagonists rather than agonists. Thus replacement of the methyl group of morphine by an allyl or cyclopropylmethyl moiety produces an antagonist. Although there are some exceptions to this rule, such as N-amylnormorphine and N-hexylnormorphine, in general a large substituent will result in antagonist activity.

We have attempted to modify the ability of biologically-active compounds to cross the blood-brain barrier by incorporating a highly polar group into the molecular structure. Thus we have shown that derivatives of the 2N atom of mianserin comprising a guanidino group show $H_1$ and 5-hydroxytryptamine activity, but show no detectable activity in the central nervous system. In contrast, a compound in which the 2N atom of mianserin was substituted with a urea group still showed pronounced central nervous system activity (Jackson et al; Clin. Ex. Pharmacol. Physiol., 1992 19 17–23 and our U.S. Pat. No. 5,049,637).

Naltrexamine and oximorphamine have been modified by incorporation of groups which are zwitterionic at biological pH in order to restrict access to the central nervous system (Botros et al; J. Med. Chem., 1989 32 2068–2071, and Portoghese, U.S. Pat. No. 4,730,048). In U.S. Pat. No. 4,730,048 the zwitterionic group was added at C6. Some of these analogues were full agonists, and one was a strong antagonist.

A bis(t-butyldimethylsiloxy)-substituted compound in which a guanidino derivative was attached to the nitrogen via a 3 carbon spacer chain was found to show no opioid activity at $\mu$-receptors in isolated guinea-pig ileum (Jackson et al, 1992). This suggested that such compounds would not have the desired activity.

Therefore there is a need for therapeutic compounds which have less activity within the central nervous system, thus having fewer undesirable side-effects, whilst at the same time having greater specificity of action on peripheral physiological mechanism. We have found that several compounds with the general formula outlined below not only have reduced central side-effects; but retain activity at desired peripheral receptors. In particular, those compounds which show activities at opioid receptors retain broad analgesic activity, contrary to current orthodoxy which teaches that the analgesic effects of opioids are mediated from the CNS. Their selectivity for peripheral opioid receptors not only makes them useful in for the treatment of pain without sedative or addictive effects, but also may make them useful for treatment of AIDS and related immune deficiency diseases.

SUMMARY OF THE INVENTION

In its broadest aspect, the invention provides an opioid compound of general formula I

[opioid-N]-[spacer]-[charged group],          I in which an opioid compound is linked via the nitrogen at position 17 to a spacer group, which in turn is linked to a charged group.

For the purposes of this specification, the term "opioid compound" is to be taken to mean a compound structurally related to morphine. The opioid compound preferably, but not necessarily, has opioid agonist or antagonist activity at opioid receptors.

The spacer can be any spacer group of dimensions approximately equivalent to an alkyl chain of 1 to 6 carbon atoms, and may for example be a straight or branched alkyl, alkenyl or alkynyl chain of 1 to 6 carbon atoms, which may optionally be susbstituted. The spacer also comprises a cyclic alkyl, alkenyl, or alkynyl group. Preferably the spacer group is unsubstituted, and more preferably is of 2 to 3 carbons atoms. The charged group may be any group which has the ability to restrict access of the compound of formula I to the central nervous system, and is preferably an amidine or guanidine group.

According to one embodiment, the present invention provides an opioid compound of general formula (II)

in which

YN— represents an organic residue obtained by removal of the R group from an opioid compound of general formula $$YN-R \quad (IIIa)$$

wherein R is H, alkyl of 1 to 6 carbon atoms, or cyclopropylmethyl, or of the general formula (IIIb)

wherein $R^4$ is methyl or ethyl, and

Y1—$NR^4$ represents the corresponding organic residue;

Z is O, S or $NR^3$;

$R^1$ is $H_1$, alkyl or aryloxyalkyl, wherein the aryl group is optionally substituted by alkyl, alkoxy, halogen, or alkyl substituted by halogen, and alkyl, alkoxy and the alkyl moiety of aryloxy alkyl have 1 to 6 carbon atoms;

$R^2$ is H or an alkyl group having 1 to 6 carbon atoms;

$R^3$ is H, alkyl, hydroxy, amino, cyano or acyl, wherein alkyl and acyl have 1 to 6 carbon atoms;

n is an integer of 1 to 6, and wherein $R^1$ and $R^3$ may together complete an addition ring; then the grouping may become a heterocyclic moiety such as 2-imidazolyl or 2-imidazolinyl:

Preferably R is $CH_3$.
Preferably n is 2 or 3.
Preferably Z is NH, and $R^1$ and $R^2$ are both H.

In order to indicate the trivalent N-atom more clearly, the structure of compounds of the formula (IIIa) may be written (IIIc)

The precursors of YN— and $Y^1NR^4$— respectively are selected from compounds which are structurally related to morphine.

Thus the precursor of YN— or $Y^1NR^4$— is preferably a compound selected from the group consisting of morphine, codeine, heroin, ethylmorphine, O-carboxymethylmorphine, O-acetylmorphine, hydrocodone, hydromorphone, oxymorphone, oxycodone, dihydrocodeine, thebaine, metopon, etorphine, acetorphine, ketobemidone, ethohe ptazine, diprenorphine (M5050), buprenorphine, phenomorphan, levorphanol, pentazocine, eptazocine and metazocine.

Preferably the precursor is morphine, codeine or buprenorphine.

In a preferred embodiment, the compound of general formula I is one of the following:

KRS-41

KRS-2-19

KRS-3-23-4

KRS-3-28

KRS-3-30-2

-continued

KRS-3-56

KRS-2-63

KRS-2-47

KRS-4-8

KRS-3-7

Typical examples of morphine-related compounds of the formula (IIIa) or (hIIc) are illustrated in Table 1. In each case the group R has been circled in order to clearly identify the residue YN— or $Y^1N^4$— as the remainder of the molecule.

The preferred precursors also include the unnamed compounds whose structures are shown in Table 1, with the nitrogen atom at position 17 indicated.

TABLE 1

Compounds with Analgesic or Related Type Activity and Some Related Structures

| R | $X_1$ | $X_2$ | Name |
|---|---|---|---|
| $CH_3$ | H | H | Morphine |
| " | $CH_3$ | H | Codeine |
| " | Et | H | Ethylmorphine |
| " | Ac | Ac | Heroin |
| " | $CH_2COOH$ | H | O-Carboxymethylmorphine |
| " | Ac | H | O-Acetylmorphine |
| " | $tBuMe_2Si$ | $tBuMe_2Si$ | "Disilyl" morphine |
| H | $tBuMe_2Si$ | $tBuMe_2Si$ | "Disilyl" normorphine |

| R | X | – or = | R' | R" | R''' | Name |
|---|---|---|---|---|---|---|
| $CH_3$ | H | = | H | H | Et | Etorphine |
| " | Ac | = | H | H | Et | Acetorphine |
| " | H | – | H | H | Et | Dihydroetorphine |
| " | Ac | – | H | H | Et | Dihydroacetorphine |
| $CH_2$-cyclopropyl | H | – | H | H | H | Diprenorphine |
| " | H | – | $CH_3$ | $CH_3$ | $CH_3$ | Buprenorphine |

| $X_1$ | $X_3$ | $X_4$ | Name |
|---|---|---|---|
| $CH_3$ | H | H | Hydrocodone |
| H | H | H | Hydromorphone |
| H | OH | H | Oxymorphone |
| $CH_3$ | OH | H | Oxycodone |
| H | H | $CH_3$ | Metopon |

TABLE 1-continued

Compounds with Analgesic or Related Type Activity and Some Related Structures

| R | Name |
|---|---|
| PhCH$_2$CH$_2$ | Phenomorphan |
| CH$_3$ | Levorphanol |

| R | Name |
|---|---|
| CH$_3$CH$_2$ | Ketobemidone |
| CH$_3$CH$_2$O | Ethoheptazine |

| R | X | Name |
|---|---|---|
| CH$_3$ | H | Eptazocine |
| Me$_2$C=CHCH$_2$— | CH$_3$ | Pentazocine |
| CH$_3$ | CH$_3$ | Metazocine |

Dihydrocodeine

TABLE 1-continued

Compounds with Analgesic or Related Type Activity and Some Related Structures

Thebaine

Thus the invention provides in a second broad aspect an opiate receptor agonist having analgesic properties and having reduced or no CNS activity. Preferably the opiate receptor agonist is a compound of general formula I or general formula II as defined above.

Where appropriate, the invention also includes pharmaceutically acceptable salts of the compounds of formula I, or formula II. A variety of pharmaceutically-acceptable salt-forming organic and inorganic acids is well known in the art.

According to a third aspect, the invention provides a method of reducing the central nervous system activity of an opioid compound, comprising the step of linking the nitrogen atom at position 17 of said compound to a spacer group, which in turn is linked to a charged group. Optionally the linkage to the charged group is via a spacer group.

According to a fourth aspect of the invention, methods for the preparation of the compounds of formula II are provided, as set out below, in which it will be appreciated that YN— may be replaced by Y$^1$NR$^4$—:

1. By the reaction of a compound of formula with a cyanamide, R$^1$NHCN, according to the equation

2. By the reaction of a compound of formula (IV) with a compound of formula wherein L is a suitable leaving group, for example CH$_3$O, CH$_3$S, CH$_3$SO$_2$, SO$_3$H, pyrazole or (3,5-dimethylpyrazol-1-yl) according to the equation Compounds of the formula (II) wherein Z is S not only possess useful therapeutic activity per se, but may also be used as intermediates for the preparation of compounds of formula II wherein Z is $NR^2$, eg.

3. By the reaction of a compound of the formula

(VI)

with $H_2S$ there is obtained an N-thiocarboxamide $YN\!-\!CSNH_2$, which may be reacted with an amine $R^1R^2NH$ according to the two-stage equation to yield compounds of the invention where Z is S and where Z is NH.

4. The N-thiocarboxamide may also be methylated, for example using $CH_3I$, to yield an isothiourea compound, which in turn may be reacted with an amine $R^1R^2NH$ to yield a compound of the invention:

5. An alternative method of synthesis of compounds of formula (II) comprises reacting an N-cyano compound of formula (VI) with methanol under acidic conditions to yield an isourea, which in turn is reacted with an amine according to the equation

6. Compounds according to formula (II) where Z is N may also be prepared, for example from the N-cyano compound of formula (VI) and the appropriate metallated residue (for example, sodamide or metallated amines):

7. Compounds of the formula (VI), most of which are also novel, and which are useful as intermediates in reactions 3, 5 and 6 above, are prepared by reacting a compound of formula (III) (see Table 1) with cyanogen bromide in a hydrocarbon solvent:

8. Compounds of general formula (IV), which are useful as intermediates in reactions 1 and 2, are prepared from the compounds of formula (III) (Table 1) by the following reactions:

Some compounds of the invention are optically active, and it will be clearly understood that both racemic mixtures and isolated stereoisomers are within the scope of the invention.

According to a fifth aspect, the invention provides a composition comprising as an effective agent a compound according to formula I, together with a pharmaceutically acceptable carrier.

Methods and pharmaceutical carriers for preparation of pharmaceutical compositions are well known in the art, as set out in textbooks such as Remington's Pharmaceutical Sciences, 17th Edition, Mack Publishing Company, Easton, Pa., USA.

According to a sixth aspect, the invention provides a method of inducing analgesia, comprising the step of administering an effective amount of a compound of the invention to a mammal in need of such treatment. The mammal may be a human, or may be a domestic, companion or zoo mammal. Preferably the mammal is a human.

The dosage to be used will depend on the nature and severity of the condition to be treated, and will be at the discretion of the attending physician or veterinarian. The most suitable dosage for a specific condition can be determined using normal clinical trial procedures.

For the purposes of this specification it will be clearly understood that the word "comprising" means "including but not limited to", and that the word "comprises" has a corresponding meaning.

BRIEF DESCRIPTION OF THE FIGURES

FIG. 1 shows dose-response curves for morphine-like activity in guinea-pig stimulated ileum preparations, using morphine as standard:

a) Compounds KRS-3-28 and KRS-3-30-2 (4 animals in each group);
b) Compounds KRS-41 and KRS-2-19.
c) Compound KRS-3-56 (3 animals in each group).

DETAILED DESCRIPTION OF THE INVENTION

The invention will now be described in detail by way of reference only to the following non-limiting examples, and to the Figures.

EXAMPLE 1

Preparation of N-Cyano Compounds, YN—CN

A solution of YN—R (0.02 mole of the base) in anhydrous benzene (20 ml) was added slowly to a stirred solution of cyanogen bromide (2.3 g) in anhydrous benzene (20 ml) in an atmosphere of nitrogen. After 24 hours, the mixture was diluted with diethyl ether (50 ml) and shaken with water (50 ml). The separated aqueous layer was back extracted with a mixture of benzene and ether (equal volumes of each, total 50 ml) and the combined organic layers dried over anhydrous potassium carbonate and then evaporated under reduced pressure. The residual solid was recrystallized from ethanol to give the N-cyano derivative YN—CN as colourless needles.

EXAMPLE 2

Preparation of Carboxamidines,

A solution of sodamide in liquid ammonia was prepared in the usual-way from metallic sodium (0.35 g) in dried liquid ammonia (150 ml) in the presence of a trace of ferric nitrate. The reaction mixture was kept at about −70° C. and moisture was rigorously excluded. The N-cyano derivative YN—CN (0.01 mol) was then added slowly, and the mixture stirred whilst dried hexamethylphosphorictriamide (HMPA) was added dropwise until the N-cyano compound began to dissolve; about 1 ml of HMPA was required. A deep brown solution was formed. The stirring was continued for 30 minutes and the solution poured cautiously into a solution of ammonium chloride (4 g) in iced water (150 ml). The resulting suspension was kept for some 30 minutes at room temperature and the solid then filtered off and washed with a little water. The residue (a) was reserved. The combined filtrate and washings were concentrated in vacuo to about 25 ml, when a second crop of solid (b) separated. The two crops (a) and (b) were combined and recrystallized from isopropanol to give the carboxyamidine hydrochloride as the colourless solid.

EXAMPLE 3

Preparation of Thiocarboxamido Derivatives, YN—CSNH$_2$

Dry hydrogen sulphide was passed through a solution of the N-cyano compound YN—CN (500 mg) in a mixture of triethylamine (0.25 ml) and pyridine (25 ml) for 24 hours. The resulting solution was poured into water (150 ml) and the mixture stirred for 30 minutes at room temperature to afford colourless crystals which were filtered off, washed with fresh water and dried in in vacuo. Recrystallization from a mixture of diethyl ether and light petroleum gave colourless needles of the desired compound.

EXAMPLE 4

Preparation of Carboxoamido Derivatives, YN—CONH$_2$

A slurry of the N-cyano compound YN—CN (0.02 moles) in aqueous hydrogen peroxide (100 Vol., 0.51 ml) and 20% aqueous sodium hydroxide (0.51 ml) was stirred for 30 minutes, during which time the reaction mixture became warm, then cooled to room temperature; some oxygen was evolved. Three portions of methanol (3×2 ml) were added to the reaction mixture, at 30 minute intervals with stirring. The mixture was warmed to 60° C. for 15 minutes, then poured into water (50 ml) to give a white precipitate which was filtered at the pump, washed with water (2×10 ml) and dried in vacuo to give the N-carboxamido derivative YN—CONH$_2$ as a colourless solid.

EXAMPLE 5

Preparation of 3,6-bis(t-butyldimethyl-siloxy)-7,8-didehydro-4,5-epoxymorphinan (3,6α-Bis[dimethyl (1,1-dimethylethyl)siloxy]-7,8-didehydro-4,5α-epoxymorphinan)

Dry, alcohol-free dichloromethane (100 ml) was added to a flask containing normorphine (5.42 g, 20 mmol), t-butyldimethylsilyl chloride(6.62 g, 44 mmol), imidazole (6.12 g, 90 mmol), and 4-dimethylaminopyridine (120 mg, 1.0 mmol). After 20 hours of stirring at room temperature, the reaction mixture was diluted with ether (200 ml), washed with water (3×200 ml), dried (Na$_2$SO$_4$), and evaporated to give a grey-yellow solid (10.11 g). Recrystallization from ethanol gave very fine grey needles (5.20 g, 52%), m.p. 105.7–107.0° C. The mother liquors were recrystallized (ethanol, twice) to give a second crop (2.45 g, 25%), m.p. 105.0–106.7° C. A small portion of the first crop was recrystallized again to give m.p. 106.2–107.2° C.

EXAMPLE 6

Preparation of 3,6-bis(t-butyldimethyl-siloxy)-7,8-didehydro-4,5-epoxy-17-methylmorphinan (O,O'-Bis-t-butyldimethylsilyl-morphine)

Ref: Neuvo, J. Chim. 1980 4 (6) 369–375

Solid t-butylchlorodimethylsilane (3.8 g, 25 mmol) was added to a stirred solution of morphine (3.0 g, 10.5 mmol) and imidazole (3.6 g, 52.9 mmol) in dimethylformamide (DMF; 20 ml) under a nitrogen atmosphere. Stirring of the reaction mixture was continued at room temperature for 2 hours, then the mixture was heated to 90° for 4 hours. The mixture was poured into water (25 ml) then extracted into dichloromethane (3×25 ml), dried (K$_2$CO$_3$) and evaporated to give a yellow oil, which crystallised on addition of a small amount of methanol. Recrystallisation from methanol gave colourless needles m.p. 118–119° C. (Lit 119–119.5° C.) (5.02 g, 93%).

EXAMPLE 7

Preparation of 3,6-bis(t-butyldimethyl-siloxy)-7,8-didehydro-4,5-epoxy-17-N-cyano-morphinan A solution of bis-silylmorphine (7.0 g, 1.36 mmol) in dry benzene (50 ml) was added dropwise to a stirred solution of cyanogen bromide (2.9 g, 27.4 mmol) in dry benzene under a nitrogen atmosphere. The stirred solution was refluxed for 4 hours, allowed to cool to room temperature, then evaporated. The solid residue was purified by rotary chromatography (SiO$_2$: 5% ethanol in chloroform), then crystallisation from methanol to give 3,6-bis(t-butyldimethyl-siloxy)-7,8-didehydro-4,5-epoxy-17-N-cyano-morphinan (6.3 g, 86%).

EXAMPLE 8

Preparation of O,O'-bis-t-butyldimethylsilyl-N-thiocarboxamidonormorphine

Cyanamide (524 mg, 1.0 mmol) and triethylamine (101 mg, 1.0 mmol) were dissolved in dry pyridine (20 ml). Dry hydrogen sulphide gas was slowly bubbled through the stirred pyridine solution for 4 hours, then the mixture was poured into water (100 ml), extracted into dichloromethane (3×20 ml), washed with water (3×20 ml), dried with $MgSO_4$, and evaporated. Recrystallisation from methanol gave colourless needles of the required O,O'-bis-t-butyldimethylsilyl-N-thiocarboxamidonormorphine (490 mg, 88%).

EXAMPLE 9

Preparation of 3,6-bis(t-butyldimethyl-siloxy)-7,8-didehydro-4,5-epoxy-17-(N-carboxamidino)-morphinan Ref: Ravi S. Garigipati, Tetrahedron Letters, Vol 31, No 14, pp 1969–1972, 1990. J. I. Levin, E. Turos and S. M. Weinrub, Synthetic Communications, 12, 989–993, 1982.

A solution of 3,6-bis(t-butyldimethylsiloxy)-7,8-didehydro-4,5-epoxy-17-N-cyano-morphinan (100 mg. 0.19 mmol) in dry benzene (2 ml) was added to a solution of methylchloroaluminium amide (prepared according to the Weinrub procedure) in benzene at room temperature. This solution was heated at 80° C. under nitrogen for 20 h. The reaction mixture was cooled, and the aluminium complex was decomposed by carefully pouring the solution into a slurry of silica gel (2.0 g) in chloroform. The mixture was stirred for 5 min and filtered. The filter cake was washed with methanol (50 mL). Evaporation of the filtrate gave a white solid (0.106 g), which was used in the next step without further purification.

EXAMPLE 10

Preparation of (5α,6α)-7,8-didehydro-4,5-epoxy-17-N-(2-carboxamidino)-morphinan-3,6, -diol. (KRS-2-19)

Ref: R. Newton, D. Reynolds, M. Finch, D. Kelly, S. Roberts, Tetrahedron Letters, No 41, 3981–82, 1979.

A slurry of 3,6-bis(t-butyldimethylsiloxy)-7,8-didehydro-4,5-epoxy-17-(N-carboxamidino-morphinan (106 mg, 0.19 mmol) in 10:1 mixture of acetonitrile and tetrahydrofuran was cooled in an ice bath, and 40% aqueous HF (0.2 mL) was added dropwise. After stirring overnight at room temperature the reaction mixture was concentrated under reduced pressure to give a light yellow solid, which was passed through a short silica gel column using methylene chloride/methanol in 8:2 ratio as the eluent to give KRS-2-19 as a white solid (0.64 g, 98%).

EXAMPLE 11

Alternative Preparation of 3,6-bis(t-butyldimethylsiloxy)-7,8-didehydro-4,5-epoxymorphinan Normorphine, prepared according to Chemical Abstracts, Vol. 54, 162f, (100 mg, 0.36 mmol) was dissolved in dry DMF (0.5 mL) and imidazole (0.0628 g, 0.92 mmol) and dimethylaminopyridine (0.07 g) was added. t-Butyldimethyl-silyl chloride was then added in small amounts at room temperature. After the addition was complete the reaction mixture was stirred at room temperature under nitrogen while being monitored by thin layer chromatography. After 10–15 min distilled water was added and the reaction mixture was extracted with methylene chloride. The methylene chloride layer was dried over potassium carbonate and evaporated under reduced pressure to give crude product, which was purified by column chromatography on silica gel using methylene chloride/methanol/ammonium hydroxide in 9:1:0.1 ratio as the eluent. (Yield= 120 mg, 65%).

EXAMPLE 12

Preparation of 3,6-bis(t-butyldimethyl-siloxy)-7,8-didehydro-4,5-epoxy-17-(N-2-cyanoethyl) morphinan Ref: J. A. Bell and C. Kenworthy, Synthesis, 650–652, 1971. 3,6-Bis(t-butyldimethylsiloxy)-7,8-didehydro-4,5-epoxymorphinan (0.26 g, 0.52 mmol) was dissolved in absolute ethanol (3 mL) and acrylonitrile (0.07 ml, 1.0 mmol) was added dropwise at room temperature. The reaction mixture was stirred at room temperature overnight, and the solvent was evaporated under reduced pressure to give a white solid (0.26 g, 90% yield).

EXAMPLE 13

Preparation of 3,6, bis(t-butyldimethyl-siloxy)-7,8-didehydro-4,5-epoxy-17-N-[(2-aminoiminomethyl)ethyl]morphinan A solution of 3,6-bis(t-butyldimethylsiloxy)-7,8-didehydro-4,5-epoxy-17-(N-2-cyanoethyl) morphinan (0.257 g, 0.46 mmol) in dry benzene (5 mL) was added to a solution of methylchloroaluminum amide in benzene at room temperature. The solution was heated at 80° C. under nitrogen for 20 h. This was worked up as before to give a white solid (0.157 g), which was used for the next step without further purification.

EXAMPLE 14

Preparation of (5α,6α)-7,8-didehydro-4,5-epoxy-17-N-[(2-aminoiminomethyl)ethyl]-morphinan-3,6-diol. (KRS-41)

The crude 3,6, bis(t-butyldimethylsiloxy)-7,8-didehydro-4,5-epoxy-17-N[(2-aminoiminomethyl)ethyl]-morphinan was deprotected using 40% HF in 10:1 mixture of acetonitrile and tetrahydrofuran as described before. The product was triturated with ethylacetate and with methanol. The remaining white precipitate was recrystallized with ethanol and water to give KRS-41 as a white powder (90 mg) in 94% yield.

EXAMPLE 15

Preparation of N-carboxamidino-7α-(1-hydroxy-1-methylethyl)-6,14-endo-ethenotetrahydro-northebaine (KRS-3-7)

N-Cyano-7α-(1-hydroxy-1-methylethyl)-6,14-endo-ethenotetrahydronorthebaine was prepared according to the method of Bentley and Hardy, J. Amer. Chem. Soc., 1967 89 3281–3292. This compound was reacted with methylchloroaluminum amide in benzene as described before. The crude product was purified by column chromatography on silica gel using methylene chloride/methanol/ammonium chloride in 6:1:0.1 ratio as the eluent to give KRS-3-7 as a white solid (56 mg. 91% yield).

EXAMPLE 16

Preparation of N[(2-aminoiminomethyl)ethyl]-7α-(1-hydroxy-1-methylethyl)-6,14-endo-ethenotetrahydronorthebaine (KRS-3-28)

7α-(1-Hydroxy-1-methylethyl)6,14-endo-ethenotetrahydronorthebaine, prepared according to the method of Bentley and Hardy (1967) op. cit., was converted to the corresponding N-2-cyanoethyl compound in 96% yield by reacting with acrylonitrile in absolute ethanol.

N-2-Cyanoethyl-7α-(1-hydroxy-1-methylethyl)-6,14-endo-ethenotetrahydronorthebaine was then reacted with methylchloroaluminum amide in benzene as described above. The crude product was purified by column chromatography on silica gel using methylene chloride/methanol/ammonium chloride in 9:1:0.1 ratio as the eluting solvent to give KRS-3-28 (125 mg, 45% yield).

EXAMPLE 17

N-Carboxamidino-7α-(1-hydroxy-1-methylethyl)-6,14-endo-ethenotetrahydro-nororipavine (KRS-3-23-4)

3-O-Acetyl-7α-(1-hydroxy-1-methylethyl)-6,14-endo-ethenotetrahydrooripavine, prepared according to the method of Bentley and Hardy, op.cit., was reacted with cyanogen bromide in dry methylene chloride to give 3-O-acetyl-N-cyano-7α-(1-hydroxy-1-methylethyl)-6,14-endo-ethenotetrahydronororipavine in 97% yield. This compound was then reacted with methylchloroaluminum amide in benzene as described above. The crude product was purified by column chromatography on silica gel using methylene chloride/methanol/ammonium chloride in 6:1:0.1 ratio as the eluting solvent to give KRS-3-23-4 as a white solid (102 g, 34% yield).

EXAMPLE 18

N-Carboxamidino-7α-(1-hydroxy-1-methylethyl)-6,14-endo-ethanotetrahydro-oripavine (KRS-3-30-2)

7α-(1-Hydroxy-1-methylethyl)-6,14-endo-ethanotetrahydro-oripavine was prepared by the method of Lewis, J. W., "Narcotic Antagonists", in Advances in Biochemical Psychopharmacology, 1974 8 123–136, Raven Press, New York. The 3-O-acetyl ester was prepared by the addition of acetic anhydride to a solution of the phenol in aqueous sodium hydroxide, and was obtained as a white solid. The O-acetyl ester was then reacted with cyanogen bromide in dry chloroform to give N-cyano-nororipavine derivative in 70% yield, which was then reacted with methychloroaluminum amide in benzene. The crude product was purified by column chromatography on silica gel using methylene chloride/methanol/ammonium hydroxide in 9:1:0.1 ratio. KRS-3-30-2 was obtained as a white powder in 30% yield.

EXAMPLE 19

N-(N'-carboxamidino-3-aminopropyl)-7α-(1-hydroxy-1-methylethyl)-6,14-endo-ethenotetrahydronororipavine (KRS 3-56)

a) Preparation of N-2-cyanoethyl-7α-(1-hydroxy-1-methylethyl)-6,14-endo-ethenotetrahydronororipavine 7α-(1-Hydroxy-1-methylethyl)-6,14-endo-ethenotetrahydronororipavine was prepared according to the method of K. W. Bentley and D. G. Hardy, Journal of the American Chemical Society, 1967 89 3281–3292. This compound was reacted with acrylonitrile in absolute ethanol as described. The crude product was purified by column chromatography on silica gel using methylene chloride/ethyl acetate/methanol in 4:4:1 ratio as the eluent.

b) Preparation of 3-(t-butyldimethylsiloxy)-N-2-cyanoethyl-7α-(1-hydroxy-1-methylethyl)-6,14-endo-ethenotetrahydro-nororipavine Solid t-butyldimethylsilyl chloride (0.035 g, 0.227 mmol) was added in small amounts to a stirred solution of N-2-cyanoethyl-7α-(1-hydroxy-1-methylethyl)-6,14-endo-ethenotetrahydronororipavine (80 mg, 0.189 mmol), imidazole (0.015 g, 0.227 mmol) and 4-dimethylaminopyridine (0.005 g) in anhydrous dimethylformamide (0.5 ml) under a nitrogen atmosphere. After stirring for 1 h at room temperature distilled water (10 ml) was added to the reaction mixture and the mixture was extracted with methylene chloride. The organic layer was dried over potassium carbonate and evaporated under reduced pressure. The solid formed was purified by column chromatography on silica gel, using ethyl acetate/X4 in 1:1 ratio as the eluent. (Yield=79 mg, 78%)

c) Preparation of 3-(t-butyldimethylsiloxy)-N-(3-aminopropyl)-7α-(1-hydroxy-1-methylethyl)-6,14-endo-ethenotetrahydro-nororipavine.

3-(t-butyldimethylsiloxy)-N-2-cyanoethyl-7Oα-(1-hydroxy-1-methylethyl)-6,14-endo-ethenotetrahydro-nororipavine (100 mg, 0.186 mmol) in dry ethyl ether (2 ml) was added dropwise to lithium aluminium hydride (0.008 g, 0.223 mmol) in dry ether (2 ml). After stirring for 3 h at room temperature wet ether followed by 10% NaOH (1 ml) was added to the reaction mixture. The solution was filtered and the white precipitate was washed with ether. The ether layer was evaporated under reduced pressure to give the amine as a white solid (99 mg, 98%).

d) Preparation of 3-(t-butyldimethylsiloxy)-N-(N-carboxamidino-3-aminopropyl)-7α-(1-hydroxy-1-methylethyl)-6,14-endo-ethenotetrahydronororipavine Ref: Michael S. Bernatowicz, Youling Wu and Gary R. Matsueda, Journal of Organic Chemistry, 1992 57 2497–2502

To a mixture of 3-(t-butyldimethylsiloxy)-N-(3-aminopropyl)-7α-(1-hydroxy-1-methylethyl)-6,14-endo-ethenotetrahydronororipavine (0.196 g, 0.37 mmol), diisopropylethylamine (0.065 ml, 0.37 mmol) and 1H-pyrazole-1-carboxamidine hydrochloride (0.055 g, 0.37 mmol) was added anhydrous dimethylformamide (2 ml), and the reaction mixture was stirred at room temperature under nitrogen for overnight. The reaction mixture was evaporated to dryness under reduced pressure, and the crude product was chromatographed on silica gel. (Yield=0.191 g, 88%).

e) Preparation of N-1(N'-carboxamidino-3-aminopropyl)-7α-(1-hydroxy-1-methylethyl)-6,14-endo-ethenotetrahydro-nororipavine (KRS 3-56)

40% HF (0.3 ml, 0.0065mol) was added dropwise to 3-(t-butyldimethylsiloxy)-N-(N'-aminoiminomethyl-aminopropyl)-7α-(1-hydroxy-1-methylethyl)-6,14-endo-ethenotetrahydronororipavine (0.191 g, 0.3 mmol) in 10:1 mixture of acetonitrile/tetrahydrofuran (10 ml), and the reaction mixture was stirred overnight at room temperature. The white precipitate formed was filtered and was washed with acetonitrile and then with methanol to give KRS 3-56 as a white solid (0.135 g, 96%).

EXAMPLE 20

5α,6α-7,8-didehydro-4,5-epoxy-3-methoxy-17-N-[(2-aminoiminomethyl)ethyl]morphinan (KRS-2-63)

a) Preparation of 7,8-didehydro-4,5-epoxy-17-(N-2-cyanoethyl)morphinan-3,6-diol

Acrylonitrile (0.03 mL, 0.44 mmol) was added dropwise to normorphine (0.1 g, 0.37 mmol) in absolute ethanol (2 mL) at room temperature. The reaction mixture was stirred at room temperature overnight and the solvent was evaporated under reduced pressure. The crude product was chromatographed on silica gel using ethylacetate and hexane in 3:1 ratio as the eluent (yield=86 mg, 71%).

b) Preparation of 7,8-didehydro-4,5-epoxy-3-methoxy-17-(N-2-cyanoethyl)morphinan-6-ol 7,8,-Didehydro-4,5-epoxy-17-(N-2-cyanoethyl)-morphinan-3,6-diol (86 mg, 0.265 mmol) was suspended in dry acetone (2 mL), and anhydrous potassium carbonate (0.037 g, 0.27 mmol) was added, followed by methyl iodide (0.025 ml, 0.39 mmol). After refluxing for 5 h the solvent was evaporated under reduced pressure and the crude product was purified by column chromatography on silica gel using ethylacetate and hexane in 2:1 ratio as the eluting solvent (yield=70 mg, 78%).

c) Preparation of 6-t-butyldimethylsiloxy-7,8-didehydro-4,5-epoxy-3-methoxy-17-(N-2-cyanoethyl)morphinan 7,8-Didehydro-4,5-epoxy-3-methoxy-17-(N-2-cyanoethyl)morphinan-6-ol (50 mg, 0.15 mmol) was dissolved in dry dimethylformamide (0.5 mL), and imidazole (11.1 mg, 0.16 mmol) and dimethylaminopyridine (20 mg) was added. t-Butyldimethylsilyl chloride (24.1 mg, 0.16 mmol) was then added at room temperature under nitrogen atmosphere. After stirring for 2 h at room temperature, distilled water was added and the reaction mixture was extracted with methylene chloride. The methylene chloride layer was dried with potassium carbonate and evaporated under reduced pressure to give the crude product, which was purified by column chromatography on silica gel using ethylacetate/hexane in 3:1 ratio as the eluent (yield=50 mg, 73%).

d) Preparation of 6-t-butyldimethylsiloxy-7,8-didehydro-4,5-epoxy-3-methoxy-17-N-[(2-aminoiminomethyl)ethyl]-morphinan A solution of 6-t-butyldimethylsiloxy-7,8-didehydro-4,5-epoxy-3-methoxy-17-(N-2-cyanoethyl)morphinan (50 mg, 0.11 mmol) in dry benzene (2 mL) was added to a solution of methylchloroaluminum amide in benzene at room temperature. The solution was heated at 80° C. under nitrogen for 20 h. The reaction mixture was worked up as before to give a light brown solid, which was purified by column chromatography on silica gel using methylene chloride/methanol/ammonia in 9:1:0.1 ratio to give the product as a white solid (yield=44 mg, 85%).

e) Preparation of 5α,6α-7,8-didehydro-4,5-epoxy-3-methoxy-17-N-[(2-aminoiminomethyl)ethyl]morphinan (KRS-2-63)

6-t-Butyldimethylsiloxy-7,8-didehydro-4,5-epoxy-3-methoxy-17-N-[(2-aminoiminomethyl-ethyl)morphinan (44 mg, 0.09 mmol) was dissolved in a mixture of acetonitrile and tetrahydrofuran (2.5 mL/0.25 mL) and the solution was cooled in an ice bath. To this 0.1 mL of 40% HF was added dropwise, and the mixture was stirred for 2 h at room temperature. The white precipitate formed was filtered and washed with acetonotrile to give KRS-2-63 as the fluoride salt (yield=34 mg, 96%).

EXAMPLE 21

N-(aminoiminomethylaminopropyl)-7α-(1-hydroxy-1-methylethyl)-6,14-endo-ethanotetrahydronororipavine (KRS-4-8)

(a) Preparation of N-cyanoethyl-7(-(1-hydroxy-1-methylethyl)-6,14-endo-ethanotetrahydronorpripavine 7α-(1-Hydroxy-1-methylethyl)-6,14-endo-ethanotetrahydronororipavine was prepared according to the method of Lewis (J. W. Lewis: Narcotic Antagonists, in Advances in Biochemical Psychopharmacology, Vol. 8 edited by M. C. Braude, L. S. Harris, E. L. May, J. P. Smith and J. E. Villarreal. Raven Press, New York 1974). This compound was reacted with acrylonitrile in absolute ethanol as described. The crude product was purified by column chromatography on silica gel using ethyl acetate/hexane in 1:1 ratio as the eluent.

(b) Preparation of 3-(t-butyldimethylsiloxy)-N-cyanoethyl-7α-(1-hydroxy-1-methylethyl)-6,14-endo-ethanotetrahydro-nororipavine N-cyanoethyl-7α-(1-hydroxy-1-methylethyl)-6,14-endo-ethanotetrahydronororipavine was reacted with t-butyldimethylsilylchloride as described for KRS-3-56. The crude product was purified by column chromatography on silica gel, using ethylacetate/hexane in 2:1 ratio as the eluent.

c) Preparation of 3-(t-butyldimethylsiloxy)-N-aminopropyl-7α-(1-hydroxy-1-methylethyl)-6,14-endo-ethanotetrahydro-nororipavine 3-(t-butyldimethylsiloxy)-N-cyanoethyl-7α-(1-hydroxy-1-methylethyl)-6,14-endo-ethanotetrahydro-nororipavine (0.11 g, 0.204 mmol) in dry ethyl ether (2 ml) was added dropwise to a suspension of lithium aluminum hydride (0.093 g, 2.45 mmol) in dry ethyl ether (2 ml). After stirring for 3 h at room temperature, wet ether (5 ml) followed by 10% sodium hydroxide (1 ml) was added to the reaction mixture. The solution was filtered, and the white precipitate was washed with ether. The filtrate was evaporated under reduced pressure to give the amine as a clear liquid (70 mg, 63%).

d) Preparation of 3-(t-butyldimethylsiloxy)-N-(aminoimino-methylaminopropyl)-7α-(1-hydroxy-1-methylethyl)-6,14-endo-ethanotetrahydronororipavine Anhydrous dimethylformamide (0.5 ml) was added to a mixture of 3-(t-butyldimethylsiloxy)-N-aminoprdpyl-7α-(1-hydroxy-1-methylethyl)-6,14-endo-ethanotetrahydro-nororipavine (70 mg, 0.129 mmol), diisopropylethylamine (0.022 ml, 0.129 mmol) and 1H-pyrazole-1-carboxamidine in hydrochloride (0.019 g, 0.129 mmol), and the reaction mixture was stirred overnight at room temperature under nitrogen. The solvents were evaporated under reduced pressure, and the crude product was chromatographed on silica gel (yield=57 mg, 76%).

e) Preparation of N-(aminoiminomethylaminopropyl)-7α-(1-hydroxy-methylethyl)-6,14-endo-ethanotetrahydronororipavine (KRS-4-8)

40% HF (0.2 ml, 0.004 mol) was added dropwise to 3-(t-butyldimethylsiloxy)-N-(aminoiminomethylaminopropyl)-7α-(1-hydroxy-1-methylethyl)-6,14-endo-ethanotetrahydro-nororipavine (57 mg, 0.097 mmol) in a 10:1 mixture of acetonitrile/tetrahydrofuran (10 ml), and the reaction mixture was stirred overnight at room temperature. The white precipitate formed was filtered, and was washed with acetonitrile and then with methanol to give KRS-4-8 as the fluoride salt (44 mg, 96% yield).

EXAMPLE 22

Synthesis of (5α,6α)-7,8-didehydro-4,5-epoxy-17-(N-aminoiminomethylaminopropyl)morphinan-3,6-diol (KRS-2-47)

Preparation of 3,6-bis(t-butyldimethylsiloxy)-7,8-didehydro-4,5-epoxy-17-aminopropylmorphinan A solution of 3,6-bis(t-butyldimethylsiloxy)-7,8-didehydro-4,5-epoxy-17-cyanoethylmorphinan (200 mg, 0.36 mmol) in dry ethyl ether (5 ml) was added dropwise to a suspension of lithium aluminum hydride (0.13 g, 3.6 mmol) in dry ethyl ether (5 ml). After stirring for 3 h at room temperature the reaction mixture was added wet ether followed by 10% sodium hydroxide (1.5 ml). The solution was filtered, and the white precipitate was washed with ether.

The ether layer was evaporated under reduced pressure to give the amine as a clear liquid (yield=0.2 g, 99%).

Preparation of 3,6-bis(t-butyldirnethylsiloxy)-7,8-didehydro-4,5-epoxy-17-(N-aminoiminomethylaminopropyl)-morphinan Anhydrous dimethylformamide (2 ml) was added to a mixture of 3,6-bis(t-butyldimethylsiloxy)-7,8-didehydro-4,5-epoxy-17-aminopropylmorphinan (0.2 g, 0.359 mmol), diisopropylethylamine (0.07 ml, 0.39 mmol), and 1H-pyrazole-1-carboxamidine hydrochloride (0.06g, 0.39 mmol) and the reaction mixture was stirred overnight at room temperature under nitrogen. The reaction mixture was evaporated to dryness under reduced pressure, and the crude product was chromatographed on silica gel (yield=0.155 g, 72%).

Preparation of (5α,6α)-7,8-didehydro-4,5-epoxy-17-(N-aminoiminomethylaminopropyl)morphinan-3,6-diol (KRS-2-47)

3,6-bis(t-butyldimethylsiloxy)-7,8-didehydro-4,5-epoxy-17-(N-aminoiminomethyl-aminopropyl)morphinan was deprotected using 40% HF in a 10:1 mixture of acetonitrile and tetrahydrofuran as described before. The precipitate was filtered and washed with acetonitrile, methylenechloride followed by methanol. KRS-2-47 was obtained as a white powder in 73% yield (70 mg).

EXAMPLE 23

Analgesic Activity

We have found evidence that these compounds have analgesic activity by showing stereoselectivity for peripheral opioid receptors. Thus low subcutaneous or intraperitoneal doses of N-methylnalorphninium iodide (10–300 µg/kg) showed analgesic activity in the mouse test of Hendershot and Forsaith (J. Pharmacol. Exp. Ther., 1959 125 237–240) and in the rat inflamed paw test of Randall in and Selitto (Archs. Int. Pharmacodyn. Ther., 1957 111 409–419), whereas N-allylmorphinium iodide given in doses of 10 mg/kg was found to be inactive in both tests. S-methyllisothiocarbamoyl norheroin iodide was also active in both tests after administration of doses of 1–3 mg/kg.

Compound KRS-41 (Example 16) was tested for analgesic activity in two mouse analgesia models. In the first test, the test substance was administered to groups of 5 ICR derived male mice weighing 22±2 g one hour before subplantar injection of formalin (0.02 ml, 1% solution). Reduction of the induced hind paw licking time recorded during the following 20 to 30 minute period by 50% or more indicates analgesic activity. Table 2 below shows that KRS-41 has analgesic activity at 3 times the morphine concentration, which is consistent with the relative opiate receptor activities discussed below in Example 23.

TABLE 2

| Treatment | % Reduction in Hind Paw Licking time |
|---|---|
| Vehicle (5% DMSO/saline) | 0 |
| Morphine HCl (10 mg/kg) | 100 |
| KRS-41 (10 mg/kg) | 12 |
| KRS-41 (30 mg/kg) | 75 |

In the second test, the test substance was administered to groups of 3 ICR derived male mice weighing 22±2 g 30 minutes before injection of PQ (2 mg/kg). Reduction in the number of writhes by 50% or more per group of animals observed during the 5 to 10 minute period after PQ administration, relative to a vehicle treated control group, indicates analgesic activity. Table 3 below shows that KRS-41 has analgesic activity at 5 times the morphine concentration.

TABLE 3

| Treatment | % Reduction in Writhes |
|---|---|
| Vehicle (5% DMSO/saline) | 0 |
| Morphine HCl (3 mg/kg) | 87, 73 (two tests) |
| KRS-41 (3 mg/kg) | 18 |
| KRS-41 (15 mg/kg) | 93 |

EXAMPLE 24

Guinea Pig Stimulated Ileum Preparation

Five compounds, KRS-41 (Example 16), KRS-2-19 (Example 12), KRS-3-28 (Example 18), KRS-3-30-2 (Example 20) and KRS 3-56 (Example 21) were tested for opiate activity in a standard guinea-pig stimulated ileum assay, using morphine as a standard.

Male Monash strain guinea-pigs were killed and the ileum removed. Segments (approxm. 1.5–2.5 cm) were mounted on tissue holders with in-built stimulating electrodes, and set up in 5 ml isolated organ baths containing Krebs solution of the following composition (mM): NaCl 118.4; KCl 4.1; $MgSO_4.7H_2O$ 1.2; $KH_2PO_4$ 1.2; $NaHCO_3$ 25; glucose 11.1; $CaCl_2.2H_2O$ 2.5. The Krebs solution was bubbled with carbogen (95% $O_2$, 5% $CO_2$), and the preparations maintained at 37° C. under 1 gram resting tension. The tissues were, stimulated transmurally using single pulses of 0.5 ms duration at 0.2 Hz and 40 V from a Grass SD9 stimulator, and allowed to equilibrate under these conditions before the addition of drugs.

Figure 1A:
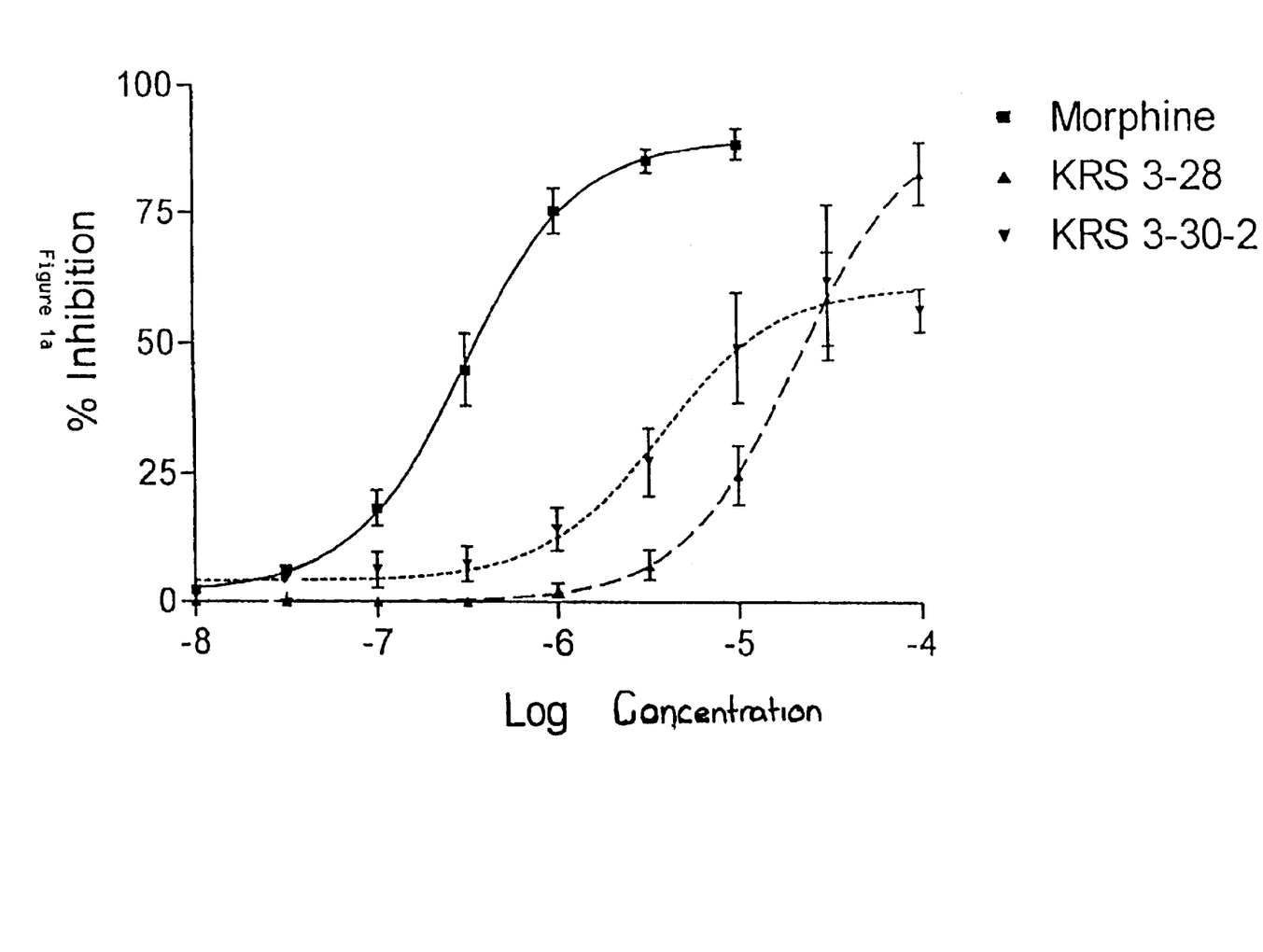

Cumulative dose-response curves to morphine (using increments of a half log unit) were obtained before obtaining cumulative dose-response curves to the test compounds. The results are shown in FIG. 1.

Figure 1B:
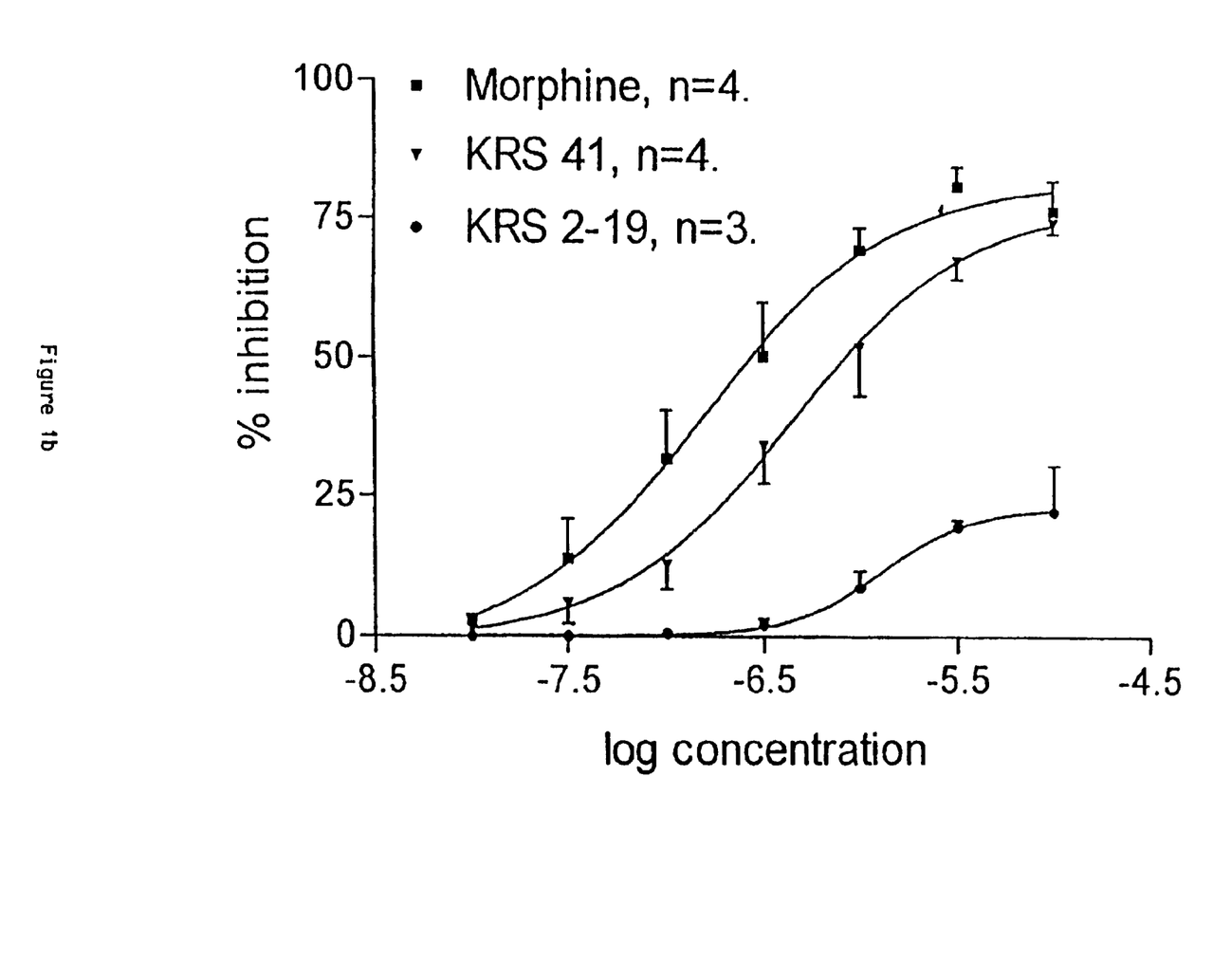
Figure 1C:
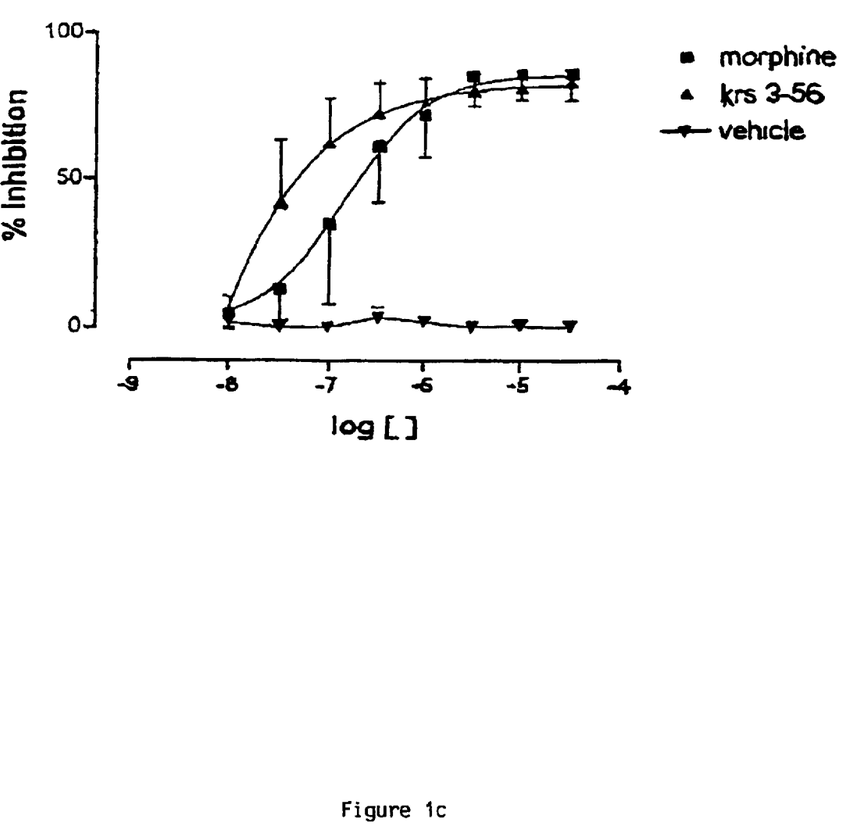

Surprisingly, KRS-41 showed excellent activity compared to morphine (FIG. 1b). This compound has an aminoiminoethyl substituent on the tertiary N atom, and was expected to have either no activity or antagonist activity. KRS-4-8 gave results similar to those observed with buprenorphine. KRS 3-56 (FIG. 10) also showed even more striking activity, with a potency of approximately 6 times that of morphine, and was a full agonist of the µ opiate receptor. KRS-2-47 is expected to give similar results.

Although KRS-3-28 had low potency compared to morphine, its activity in this assay is comparable to that of codeine. Codeine is metabolized in vivo to morphine, so its effect after oral administration is comparable to that of morphine given by injection. KRS-3-28 is expected to metabolize in similar fashion after oral administration or parenteral injection to give a buprenorphine-like compound.

In contrast, KRS-2-19 (FIG. 16) and KRS-3-30-2 (FIG. 1a) showed only partial morphine agonist activity. It therefore appears that a spacer group in which n is 2 results in stronger opiate activity than a spacer in which n is 1.

KRS-2-63 showed partial agonist activity, but would be expected to be converted in vivo by demethylase enzymes in the liver to KRS-41, in a similar manner to metabolism of codeine. Similar results would be expected for other compounds of the invention with a methoxy group at carbon 3.

EXAMPLE 25

Effect of KRS 3-56 and KRS-41 on the Central Nervous System

The effects of compounds KRS-3-56 and KRS-41 on the central nervous system were compared with that of morphine using a standard Irwin test (Irwin, S.; Psychopharmacologic (Berlin), 1968 13 222–257). The relevant results are shown in Tables 4 and 5.

TABLE 4

| Test | Vehicle | Morphine 10 mg/kg |
|---|---|---|
| Tail elevation | 2.5 ± 0.7 | 7.0 ± 0.7 |
| Respiratory rate | 5.6 ± 0.2 | 4.1 ± 0.3 |
| Positional Passivity | 4.7 ± 0.3 | 8.7 ± 0.4 |
| Grip strength | 5.1 ± 0.4 | 3.7 ± 0.3 |
| Corneal reflex | 4.5 ± 0.2 | 2.9 ± 0.2 |

TABLE 5

| Test | Vehicle | KRS-41 30 mg/kg | KRS-3-56 3 mg/kg |
|---|---|---|---|
| Tail elevation | 4.4 ± 0.2 | 2.0 ± 0.4 | 2.4 ± 0.4 |
| Respiratory rate | 5.1 ± 0.2 | 5.1 ± 0.2 | 5.4 ± 0.2 |
| Positional Passivity | 4.7 ± 0.2 | 4.7 ± 0.3 | 5.4 ± 0.5 |
| Grip strength | 5.0 ± 0.3 | 5.1 ± 0.4 | 5.1 ± 0.2 |
| Corneal reflex | 4.9 ± 0.1 | 4.9 ± 0.1 | 4.8 ± 0.1 |

These results indicate that the compounds of the invention, while retaining the analgesic activity of morphine, are non-sedating and do not cause respiratory depression. It is believed that this results from exclusion of the compounds from the central nervous system.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

What is claimed is:

1. A compound having the formula:

(YN)-(spacer)-(amidine or guanidine group) or wherein (YN) is an organic residue obtained by the removal of R, from an opioid of the formula YN—R, said opioid selected from the group consisting of morphine, codeine, heroin, ethylmorphine, O-carboxymethylmorphine, O-acetylmorphine, hydrocodone, hydromorphone, oxymorphone, oxycodone, dihydrocodcine, thebaine, metopon, ethorphine, acetorphine, diprenorphine (M5050), buprenorphine, phenomorphan, levorphanol, ethoheptazine, ketobemidone, dihydroetorphine and dihydroacetorphine R of YN—R is H, phenethyl, cyclopropylmethyl, or an alkyl of 1–6 carbon atoms;

(spacer) is a group linking YN to an amidine or guanidine group, wherein YN and said amidine or guanidine group are separated by 1 to 6 carbon atoms; and (amidine or guanidine group) is a group of the formula in which $R^1$ is H, alkyl or aryloxyalkyl, wherein the aryl group is optionally substituted by alkyl, alkoxy, halogen, or alkyl substituted by halogen, and alkyl, alkoxy and the alkyl moiety of aryloxy alkyl have 1 to 6 carbon atoms;

$R^2$ is H or an alkyl group having 1 to 6 carbon atoms;

$R^3$ is H, alkyl, hydroxy, amino, cyano or acyl, wherein alkyl and acyl have 1 to 6 carbon atoms; or $R^1$ and $R^3$ together complete a heterocyclic ring having two nitrogen atoms, or a pharmaceutically acceptable salt thereof, wherein said compound acts as an analgesic that has reduced sedative or addictive effect in comparison to any opioid of formula YN—R wherein YN of YN—R is identical to YN of said compound.

2. A compound according to claim 1, in which the spacer is a straight or branched alkyl, alkenyl or alkynyl chain of 1 to 6 carbon atoms.

3. A compound according to claim 1, in which the spacer is a cyclic alkyl, alkenyl or alkynyl group.

4. A compound according to claim 1, in which the spacer group is of 2 to 3 carbon atoms.

5. A compound according to claim 1, of formula:

wherein (YN) is an organic residue obtained by the removal of R, from an opioid of the formula YN—R, said opioid selected from the group consisting of morphine, codeine, heroin, ethylmorphine, O-carboxymethylmorphine, O-acetylmorphine, hydrocodone, hydromorphone, oxymorphone, oxycodone, dibydrocodeine, thebaine, metopon, ethorphine, acetorphine, diprenorphine (M5050), buprenorphine, phenomorphan, levorphanol, ethoheptazine, ketobemidone, dihydroetorphine and dihydroacetorphine R of YN—R is H, phenethyl, cyclopropylmethyl, or an alkyl of 1–6 carbon atoms;

in which $R^1$ is H, alkyl or aryloxyalkyl, wherein the aryl group is optionally substituted by alkyl, alkoxy, halogen, or alkyl substituted by halogen, and alkyl, alkoxy and the alkyl moiety of aryloxy alkyl have 1 to 6 carbon atoms;

$R^2$ is H or an alkyl group having 1 to 6 carbon atoms;

$R^3$ is H, alkyl, hydroxy, amino, cyano or acyl, wherein alkyl and acyl have 1 to 6 carbon atoms; or

$R^1$ and $R^3$ together complete a heterocyclic ring including two nitrogen atoms; and n is an integer of 1 to 6;

or a pharmaceutically acceptable salt thereof.

6. A compound according to claim 5, in which $R^1$ and $R^3$ together complete a heterocyclic ring having two nitrogen atoms.

7. A compound according to claim 6, in which the heterocyclic moiety is a 2-imidazolyl or 2-imidazolinyl group of formula:

8. A compound according to claim 6 or claim 7, in which $R^2$ is $CH_3$.

9. A compound according to claim 6, in which n is 2 or 3.

10. A compound according to claim 5, in which $R^1$ and $R^2$ are both H.

11. A compound according to claim 5, in which the opioid is morphine, codeine or buprenorphine.

12. A compound according to claim 1, said compound selected from the group consisting of

-continued

-continued

13. A method for the preparation of a compound of formula:

wherein (YN) is an organic residue obtained by the removal of, R, from an opioid of the formula YN—R, said opioid selected from the group consisting of morphine, codeine, heroin, ethylmorphine, O-carboxymethylmorphine, O-acetylmorphine, hydrocodone, hydromorphone, oxymorphone, oxycodone, dihydrocodeine, thebaine, metopon, ethorphine, acetorphine, diprenorphine (M5050), buprenorphine, phenomorphan, levoiphanol, ethoheptazine, ketobemidone, dihydroetorphine and dihydroacetorphine R of YN—R is H, phenethyl, cyclopropylmethyl, or an alkyl of 1–6 carbon atoms;

in which $R^1$ is H, alkyl or aryloxyalkyl, wherein the aryl group is optionally substituted by alkyl, alkoxy, halogen, or alkyl substituted by halogen, and alkyl, alkoxy and the alkyl moiety of aryloxy alkyl have 1 to 6 carbon atoms; and n is an integer of 1 to 6;

comprising the step of reacting a compound having the formula

YN—(CH$_2$)$_n$—NH$_2$ or

YN—H with a cyanamide of formula $R^1$NHCN.

14. A method for the preparation of a compound of formula:

wherein (YN) is an organic residue obtained by the removal of, R, from an opioid of the formula YN—R, said opioid selected from the group consisting of morphine, codeine, heroin, ethylmorphine, O-carboxymethylmorphine, O-acetylmorphine, hydrocodone, hydromorphone, oxymornbone, oxycodone, dihydrocodeine, thebaine, metopon, ethorphine, acetorphine, diprenorphine (M5050), buprenorphine, phenomorphan, levorphanol, ethoheptazine, ketobemidone, dihydroetorphine and dihydroacetorphine R of YN—R is H, phenethyl, cyclopropylmethyl, or an alkyl of 1–6 carbon atoms;

in which $R^1$ is H, alkyl or aryloxyalkyl, wherein the aryl group is optionally substituted by alkyl, alkoxy, halogen, or alkyl substituted by halogen, and alkyl, alkoxy and the alkyl moiety of aryloxy alkyl have 1 to 6 carbon atoms;

$R^2$ is H or an alkyl group having 1 to 6 carbon atoms; and n is an integer of 1 to 6;

comprising the step of reacting a compound of formula

YN—(CH$_2$)$_n$—CN or

YN—CN with a metallated residue containing —NR$^1$R$^2$.

15. A composition comprising a compound according to claim 1, together with a pharmaceutically acceptable carrier.

16. A method of inducing analgesia, comprising the step of administering an effective amount of a compound according to claim 1 to a mammal in need of such treatment.

17. A method according to claim 16, in which the mammal is a human.

18. A method of inducing analgesia, comprising the step of administering an effective amount of a compound according to claim 5 to a mammal in need of such treatment.

19. A method according to claim 18, in which the mammal is a human.

20. A composition comprising a compound according to claim 5, together with a pharmaceutically acceptable carrier.

21. A method of inducing analgesia in a mammal, said method comprising administration of a pharmaceutical composition of claim 15 in amounts effective to induce said analgesia to a mammal in need thereof.

22. A method for the preparation of a compound of formula:

wherein (YN) is an organic residue obtained by the removal of, R, from an opioid of the formula YN—R, said opioid selected from the group consisting of morphine, codeine, heroin, ethylmorphine, O-carboxymethylmorphine, O-acetylmorphine, hydrocodone, hydromorphone, oxymorphone, oxycodone, dihydrocodeine, thebaine, metopon, ethorphine, acetorphine, diprenorphine (M5050), buprenorphine, phenomorphan, levorphanol, ethoheptazine, ketobemidone, dihydroetorrhine and dihydroacetorphine R of YN—R is H, phenethyl, cyclopropylmethyl, or an alkyl of 1–6 carbon atoms;

in which

R¹ is H, alkyl or aryloxyalkyl, wherein the aryl group is optionally substituted by alkyl, alkoxy, halogen, or alkyl substituted by halogen, and alkyl, alkoxy and the alkyl moiety of aryloxy alkyl have 1 to 6 carbon atoms; and n is an integer of 1 to 6;

comprising the step of reacting a compound having the formula

YN—(CH₂)ₙ—NH₂ or

YN—H with a compound of formula (V)

(V)

wherein R¹ is as defined above, and

L is a leaving group.

* * * * *